United States Patent

Kawai et al.

Patent Number: 5,939,542
Date of Patent: Aug. 17, 1999

[54] DETECTION OF HLA-DR

[75] Inventors: Shintaro Kawai; Shinji Maekawajiri; Hirotaka Nakamoto, all of Osaka, Japan

[73] Assignee: Wakunaga Seiyaku Kabushiki Kaisha, Osaka, Japan

[21] Appl. No.: 08/931,072

[22] Filed: Sep. 15, 1997

Related U.S. Application Data

[63] Continuation-in-part of application No. 08/618,421, Mar. 8, 1996, abandoned.

[30] Foreign Application Priority Data

Mar. 10, 1995 [JP] Japan ........................ 7-51437

[51] Int. Cl.$^6$ .................................... C07H 21/04
[52] U.S. Cl. ........................ 536/24.31; 536/24.3
[58] Field of Search ................ 536/24.31, 24.3

[56] References Cited

FOREIGN PATENT DOCUMENTS

97/46700  12/1997  WIPO .

*Primary Examiner*—Kawai Lau
*Attorney, Agent, or Firm*—Oblon, Spivak, McClelland, Maier & Neustadt, P.C.

[57] ABSTRACT

A probe set is provided which can assay larger amounts of samples in a simpler manner and enables typing of all HLA-DR types currently known to be present in Japanese.

The probe set comprises part or all of oligonucleotides having the following sequences 1 to 16 or complementary strands thereof:

sequence 1: CGGTTGCTCGGAAAGATGCATC sequence 2: ACACTCCCTCTTTGGCTG sequence 3: GGCCGGGTGGACAACTAC sequence 4: ATGTTTAACCTGCTCCAA sequence 5: CCTGATGAGGAGTACTGGAA sequence 6: AGCTACTGCGCTTCGAC sequence 7: CGTAGAGTACTCCAAGAA sequence 8: CTTATACTTACCCTGCCA sequence 9: AGACAGGCGGGCCCT sequence 10: TCAAACTTATCCTGCTTC sequence 11: AAACTTAACCTCCTCCAA sequence 12: ACTCTACGTCTGAGTGTC sequence 13: ACGGGTGAGTGTTATTTC sequence 14: GACCTCCTGGAAGACAGG sequence 15: ACATCCTGGAAGACGAGC sequence 16: CCCGTAGTTGTGTCTGCA.

1 Claim, No Drawings

DETECTION OF HLA-DR

CROSS-REFERENCE TO RELATED APPLICATIONS

This application is a continuation-in-part of U.S. application Ser. No. 08/618,421 filed on Mar. 8, 1996, now abandoned.

BACKGROUND OF THE INVENTION

Field of the Invention

The present invention relates to a group of probes for HLA (human leukocyte antigens) typing. More particularly, the present invention relates to a group of probes for DNA typing of HLA-DR antigen.

Background Art

In the organ transplantation, the degree of coincidence in HLA type between a donor and a recipient of an organ has a great influence on the results of the transplantation. When the HLA type of the donor is not coincident with that of the recipient, problems occur including that rejection makes the take of the organ by the recipient impossible and that immunocytes derived from the donor cause GVHD resulting in exposure of the recipient to danger of life. Further, correlation between the incidence of certain diseases, such as diabetes, and the HLA type has been reported. Thus, HLA typing has becomes more important with an advance of medical technology.

HLA typing has been performed using antibodies. The source of the antibodies, however, is limited to a multiparous woman. Further, it is difficult to obtain monoclonal antibodies. Thus, large amounts of high-quality monoclonal antibodies cannot be stably provided. This problem is significant especially in HLA class II antigens.

On the other hand, instead of the traditional typing method (serological method) using antibodies, DNA typing method has stable specificity and further no limitation on the supply of assay reagents. Therefore, various DNA typing methods have been proposed. Furthermore, a network for the transplantation of organs, including marrow and kidney, has spread in all the world, including JAPAN MARROW DONOR PROGRAM. DNA typing for routine used as alternatives to serological method is required.

PCR-PFLP, PCR-SSO, PCR-SSP, PCR-SSCP and other methods have been proposed ("KON-NICHI NO ISHOKU," VOL. 7, SUPPL, 1994). Further, in International HLA Workshop (11th, 1991), standard reaction conditions, primers, and probes have been determined for the PCR-SSO method.

Despite the above various proposals, simpler DNA typing methods are required in typing laboratories.

Indispensable requirements for screening involved in activities of a bank of marrow and the like include:
(1) The procedure is simple and is suitable for typing a large numbers of samples,
(2) Almost all types existed in an object population are detectable.
(3) The level of grouping is appropriate, and the number of samples for the final test can be narrowed down, and
(4) The method can offer a good balance among working amount, cost of reagents and other factors.

The present inventors have previously proposed an HLA-DR typing method using 12 probes in the 23rd Annual meeting of The Japan Society for Immunology.

SUMMARY OF THE INVENTION

The present inventors have now found that the use of four additional probes in the previously proposed 12 probes, or their complementary strands thereto, in combination, enables more precise HLA-DR typing. The present invention has been made based on such finding.

Accordingly, an object of the present invention is to provide a probe set for HLA-DR typing in a large amount of samples in a simple manner.

Another object of the present invention is to provide a probe combination which enables typing of all types of HLA-DR antigens currently known to be present in Japanese.

The probe combination according to the present invention comprises part or all of oligonucleotides having the following sequences 1 to 16 and/or their complementary strands thereto:

sequence 1 (SEQ ID NO: 1): CGGTTGCTGGAAAGATGCATC
sequence 2 (SEQ ID NO: 2): ACACTCCCTCTTAGGCTG
sequence 3 (SEQ ID NO: 3): GGCCGGGTGGACAACTAC
sequence 4 (SEQ ID NO: 4): ATGTTTAACCTGCTCCAA
sequence 5 (SEQ ID NO: 5): CCTGATGAGGAGTACTGGAA
sequence 6 (SEQ ID NO: 6): AGCTACTGCGCTTCGAC
sequence 7 (SEQ ID NO: 7): CGTAGAGTACTCCAAGAA
sequence 8 (SEQ ID NO: 8): CTTATACTTACCCTGCCA
sequence 9 (SEQ ID NO: 9): AGACAGGCGGGCCCT
sequence 10 (SEQ ID NO: 10): TCAAACTTATCCTGCTTC
sequence 11 (SEQ ID NO: 11): AAACTTAACCTCCTCCAA
sequence 12 (SEQ ID NO: 12): ACTCTACGTCTGAGTGTC
sequence 13 (SEQ ID NO: 13): ACGGGTGAGTGTTATTTC
sequence 14 (SEQ ID NO: 14): GACCTCCTGGAAGACAGG
sequence 15 (SEQ ID NO: 15): ACATCCTGGAAGACGAGC
sequence 16 (SEQ ID NO: 16): CCCGTAGTTGTGTCTGCA.

The complementary strands to the oligonucleotides having the above sequences 1 to 16 are oligonucleotides having the following sequences 1a to 16a:

sequence 1a (SEQ ID NO: 17): GATGCATCTTTCCAGCAACCG
sequence 2a (SEQ ID NO: 18): CAGCCTAAGAGGGAGTGT
sequence 3a (SEQ ID NO: 19): GTAGTTGTCCACCCGGCC
sequence 4a (SEQ ID NO: 20): TTGGAGCAGGTTAAACAT
sequence 5a (SEQ ID NO: 21): TTCCAGTACTCCTCATACGG
sequence 6a (SEQ ID NO: 22): GTCGAAGCGCAGTAGCT
sequence 7a (SEQ ID NO: 23): TTCTTGGAGTACTCTACG
sequence 8a (SEQ ID NO: 24): TGGCAGGGTAAGTATAAG
sequence 9a (SEQ ID NO: 25): AGGGCCCGCCTGTCT
sequence 10a (SEQ ID NO: 26): GAAGCAGGATAAGTTTGA
sequence 11a (SEQ ID NO: 27): TTGGAGGAGGTTAAGTTT
sequence 12a (SEQ ID NO: 28): TGCAGACACAACTACGGG
sequence 13a (SEQ ID NO: 29): GACACTCAGACGTAGAGT sequence 14a (SEQ ID NO: 30): GAAATAACACTCAC-CCGT
sequence 15a (SEQ ID NO: 31): CCTGTCTTCCAGGAG-GTC
sequence 16a (SEQ ID NO: 32): GCTCGTCTTCCAG-GATGT The present inventors have also found that an oligonucleotide sequence (sequence 6') which is three bases longer than sequence 6 at the 3'-terminal hybridizes to DR12 but not to DR11 and DR14. Accordingly, another object of the present invention is to provide an oligonucleotide which hybridizes to DR12 but not to DR11 and DR14. The oligonucleotide probe of the present invention consists essentially of the sequence AGCTACTGCGCTTCGA-CAGC (sequence 6', SEQ ID NO: 42).

DETAILED DESCRIPTION OF THE INVENTION

The sequences used as the probe set according to the present invention comprise part or all of oligonucleotides having the sequences 1 to 16 or part or all of oligonucleotides having the sequences 1a to 16a. These sequences hybridize respectively with corresponding gene encoding HLA-DR antigens. Specifically, HLA-DR typing can be performed by determining which sequence(s) is hybridized to DNAs, preferably DNAs extracted from leukocytes, derived from a subject.

Types of HLA-DR antigens hybridized with the above sequences are tabulated below. The types of HLA-DR antigens can be assigned based on the following Table 1.

sequence 19 (SEQ ID NO: 33): CCTGATGAGGAG-TACTGGAACAG
sequence 20 (SEQ ID NO: 34): TGATGAGGAGTACTG-GAA
sequence 21 (SEQ ID NO: 35): AGTGTCTCTCCAG-TAACC
sequence 22 (SEQ ID NO: 36): AGCCCCTGCGCTTCGAC
sequence 23 (SEQ ID NO: 37): AGCTCATGCGCTTCGAC
sequence 24 (SEQ ID NO: 38): AGCTCCAGCGCTTCGAC Whether or not the above sequences hybridize with DNA samples may be confirmed under conventional conditions.

According to a preferred embodiment of the present invention, the sequence, when utilized in typing, is preferably immobilized as a single-stranded nucleic acid on a solid phase, preferably a microtiter plate by a method described in Japanese Patent Laid-Open No. 192198/1994.

In particular, a new sequence containing one or more repeated sequence unit(s) (preferably, in a tandem form) are prepared and then cloned into, for example, M13 phage or a phagemid vector (e.g., pUC118, pBSM13+, or PUCf1) to prepare a single-stranded nucleic acid. It is particularly preferred to use a single-stranded nucleic acid prepared from a vector with 5 to 200 units of the above oligonucleotide introduced thereinto. The single-stranded nucleic acid is immobilized on a solid phase.

A carrier used as the solid phase for immobilizing the single-stranded nucleic acid thereon may comprise any material and may be in any form, so far as the nucleic acid can be nonspecifically adsorbed thereon, or a functional group reactive with the nucleic acid to form a covalent bond can be introduced thereinto. Specific examples of the carrier

TABLE 1

| HLA-DR gene type | | Sequences of invention | | | | | | | | | | | | | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 |
| DR1 | *0101/0120–0102 | ● | | | | | | | | | | | | | | | ● |
| | *0103 | ● | | | | | | | | | | | | | | ● | ● |
| DR2 | *1501–1503/1601 | | | ● | | | | | | | | | | | | | ● |
| | *1602 | | | ● | | | | | | | | | | | ● | | ● |
| DR3 | *0301–0303 | | | | ● | | | ● | | | | ● | | | | | ● |
| | *0401/0403–0411/(1410) | | | | | ● | | | | | | | | | | | |
| DR4 | *0402 | | | | | ● | | | | | | | | | ● | | ● |
| | *0412 | | | | | ● | | | | ● | | | | | | | |
| DR11 | *1101/1103/1104 | | | | | | | ● | ● | | | ● | | | ● | | ● |
| | *1102 | | | | | | | ● | ● | | | ● | | | ● | | ● |
| DR12 | *1201/1202 | | | | | | ● | ● | | | | | ● | | ● | | ● |
| DR6 | *1301/1302/1304 | | | | | | | ● | | | | ● | | | ● | | ● |
| | *1303/1305–7/1401/1402/1405–1409 | | | | | | | ● | | | | ● | | | | | ● |
| | *1403 | | | | | | | ● | | ● | | ● | ● | | | | ● |
| | *1404/(0805) | | | | | | | ● | | | | | ● | | ● | | ● |
| DR7 | *0701 | | | | | | | | ● | | | | | | | | ● |
| DR8 | *0801–0804 | | | | | | | ● | | ● | | ● | | | | | ● |
| DR9 | *0901 | | | | | | | | | | ● | | | | | | ● |
| DR10 | *1001 | | | | | | | | | | | | | ● | | | ● |

●: hybridizable

According to the present invention, in the HLA-DR DNA typing, the following sequence 19 (SEQ ID NO: 33) or 20 (SEQ ID NO: 34) may be substituted for the sequence 5 (SEQ ID NO: 5), and any one of the following sequences 21 to 24 (SEQ ID NO: 35 to SEQ ID NO: 38 respectively) may be substituted for the sequence 6 (SEQ ID NO: 6). The reactivities of these sequences are somewhat inferior to that of combinations of the sequences 1 to 16 or the chains complementary strands thereto. Thus, when these oligonucleotides are used, care should be given, in the judgement of the results, to a cross reaction and other factors.

include the so-called microplates, tubes, and beads made of a polymer. The use of the microplate is particularly preferred from the viewpoint of ease of automation.

A method for immobilizing the single-stranded nucleic acid on the carrier includes a chemical bonding [Nucleic Acids Res., 15, 5373–5390 (1987)]. Specifically, the nucleic acid can be immobilized on a carrier through a chemical bond, for example, by chemically linking a carrier with an amino group introduced thereinto with the nucleic acid using a crosslinking agent, such as glutaraldehyde. Further, introduction of a functional group (for example, a primary amino group by a transamination reaction) into the nucleic acid followed by linking the nucleic acid through a suitable crosslinking agent to a functional group introduced onto a carrier is also useful.

It is also possible to immobilize the nucleic acid directly on a carrier by taking advantage of a nonspecific binding such as adsorption. In particular, when the carrier is a microplate, the adsorption efficiency can be enhanced by ultraviolet irradiation or by the addition of $MgCl_2$, (Japanese Patent Laid-Open No. 219400/1986). Other useful methods include one wherein a nucleic acid and a protein are chemically bonded or nonspecifically adsorbed to each other by a suitable method followed by immobilization of the nucleic acid on a carrier by utilizing nonspecific adsorption of the protein to the carrier.

In the present invention, conditions for hybridization of the sequence immobilized on the solid phase with a DNA sample may be suitably determined. For example, the hybridization in this stage may be fundamentally carried out by the conventional method using a membrane [B. D. Hames and S. J. Higgins, Nucleic Acid Hybridization, A Practical Approach, IRL Press (1985)].

DNA samples are preferably DNAs derived from human leukocytes. The target sequence to be detected is preferably labeled so that the hybridization thereof with the sequence of the present invention can be detected. Examples of labeling methods include (1) direct introduction of a labeling substance into the target nucleic acid, (2) synthesis of a nucleic acid corresponding to the target nucleic acid or a nucleic acid complementary to the target nucleic acid using a labeled oligonucleotide primer, and (3) synthesis of a nucleic acid corresponding to the target nucleic acid or a nucleic acid complementary to the target nucleic acid in the presence of a labeled unit nucleic acid using an oligonucleotide primer.

Preferred examples of the method (1), wherein a labeling substance is directly introduced into the target nucleic acid, include one wherein a biotin is introduced into the target nucleic acid by a photoreaction followed by detection using a streptoavidin with an enzyme bonded thereto [Nucleic Acids Res., 13, 745 (1985)] and one wherein the target nucleic acid is sulfonated followed by detection using an enzyme-labeled anti-sulfonation antibody [Proc. Natl. Acad. Sci. USA, 81, 3466–3470 (1984)]. These methods are preferred from the viewpoint of simple procedure and rapidity.

On the other hand, regarding the methods (2) and (3), amplification of a particular nucleic acid sequence [BIO/TECHNOLOGY, 8, 291 (1990)] can be utilized. These methods have drawn particular attention because they can amplify a target nucleic acid. Further, they are also advantageous in that a synthetic nucleic acid corresponding to a target nucleic acid or a synthetic nucleic acid complementary to the target nucleic acid can be labeled in a relatively simple manner. For example, according to the PCR method [Science, 230, 1350–1354 (1985)), a labeled elongation or amplification product can be obtained by utilizing a labeled primer or a labeled mononucleotide triphosphate. On the other hand, in the case of amplification utilizing Qβ replicase [BIO/TECHNOLOGY, 6, 1197 (1988)], the use of a mononucleotide triphosphate labeled in the same manner as described above can provide a labeled elongation or amplification product. Also in nucleic acid amplification methods other than described above, an elongation or amplification product can be labeled by previously labeling a mononucleotide triphosphate or an oligonucleotide incorporated by an elongation or amplification reaction. The method (2) is particularly preferred for the present invention.

The labeling substance used herein may be radioactive or non-radioactive so far as it can be detected after hybridization. However, non-radioactive labeling substances are preferred from the viewpoint of easy handling, storage stability, waste treatment and the like as well as because they can offer the effect of the present invention in the most efficient manner.

Examples of the non-radioactive labeling substance include, for example, haptens such as biotin, 2,4-dinitrophenyl group, and digoxigenin, fluorescent substances such as fluorescein and derivatives thereof (for example, fluorescein isothiocyanate (FITC)], rhodamine and derivatives thereof [for example, tetramethyl rhodamine isothiocyanate (TRITC) and Texas Red], 4-fluoro-7-nitrobenzofuran (NBDF), and dansyl, and chemiluminescent substances such as acridine. Oligonucleotides may be labeled with the above substances by any known means (see Japanese Patent Laid-Open Nos. 93098/1984 and 93099/1984). The labeling of nucleotide triphosphate may be carried out by any known means [Proc. Natl. Acad. Sci. USA, 80, 4045 (1983) and Japanese Patent Laid-Open No. 152364/1988], or alternatively commercially available products may be utilized.

According to a preferred embodiment, the labeling of the DNA sample is preferably carried out, using a labeled oligonucleotide primer, simultaneously with amplification by PCR. Further, according to the most preferred embodiment of the present invention, the following sequences 17 (SEQ ID NO: 39) and 18 (SEQ ID NO: 40) are used as the labeled primer.

Sequence 17 (SEQ ID NO: 39): CCGCTGCACTGT-GAAGCTCT

Sequence 18 (SEQ ID NO: 40): TCGTGTCCCCACAG-CACGT

The primers can prevent a non-specific reaction and amplify only genes coding HLA-DR antigens, leading to more definite typing.

In the present invention, a method for detecting the presence of a hybridization product of the sequence of the present invention with the DNA sample may be suitably selected and determined according to the kind of the label present in the target nucleic acid.

When the label present in the target nucleic acid is directly detectable, that is, when the label is, for example, a radioisotope, a fluorescent substance, or a dye, the detection step is carried out with the labeled nucleic acid linked to the solid phase or with the labeling substance bonded to the nucleic acid. Alternatively, the labeling substance may be liberated from the nucleic acid in a solution and then detected by a method suitable for the label. On the other hand, when the label is indirectly detectable, that is, when the label is a ligand in a specific binding reaction, such as biotin or hapten, the detection is carried out by a method commonly used in the detection of such a ligand, i.e., using a label, which can directly generate a signal, or a receptor (e.g., avidin or antibody) linked to an enzyme capable of catalyzing a reaction which can generate a signal.

EXAMPLES

Example 1

For each of 16 sequences specified in the following Table 1A, a single-stranded DNA containing a sequence obtained by repeating about 50 copies the sequence specified in the table was prepared according to a method disclosed in Japanese Patent Laid-Open No. 192198/1993.

Each single-stranded DNA thus prepared was immobilized on a microtiter plate as follows. The single-stranded DNA was first dissolved in a solution of 0.75M sodium chloride, 0.15M Tris-HCl, and 0.15M magnesium chloride (pH 8.0) to prepare a 4 μg/ml single-stranded DNA solution. The single-stranded DNA solution was added to a microtiter plate in an amount of 100 μl per well. The plate was covered, incubated at 37° C. for 16 hr, and washed three times with a buffer (1M sodium chloride, 0.1M Tris-HCl, 2 mM magnesium chloride, 0.1% Tween 20 (pH 9.3)).

Amplification was carried out 30 cycles by PCR, using DNAs extracted from human leukocytes as samples and the sequences 17 and 18 labeled with biotin at the 5' termini as primers. After the amplicon was denatured by heat, 5 μl of the denatured product was added to the wells, on which the single-stranded DNA was immobilized, containing 100 μl of a hybridization solution, and the wells were incubated at 58° C. for 1 hr. The solution was discarded, and 200 μl of a 3M tetramethylammonium chloride solution at 65° C. was added to the wells, and the wells were incubated at 65° C. for 5 min. The solution was discarded, and 200 μl of a 3M tetramethylammonium chloride solution at 65° C. was added to the wells again, and the wells were incubated at 65° C. for 10 min. The solution was discarded, and the wells were washed three times with 300 μl of an enzyme diluent (0.3M sodium chloride, 0.1M Tris-HCl, 2 mM magnesium chloride, 0.05% Tween 20 (pH 7.5)). The solution was discarded, 100 μl of a peroxidase-labeled avidin (Vector) diluted 5000 times with an enzyme diluent was added to the wells, and the wells were incubated at room temperature for 15 min. The solution was discarded, and the wells were washed three times with 300 μl of an enzyme diluent. A chromogenic substrate solution (1.5 mM 2,2'-adino-bis-(3-ethylbenzothiazoline-6-sulfonic acid)diammonium, a 0.2M tartrate buffer containing 0.015% $H_2O_2$ (pH 4.4)) was added to the wells, and a reaction was allowed to proceed at room temperature for 15 min. Thereafter, the absorbance was measured at 415 nm.

The results of the measurement of the absorbance for each sequence are tabulated below. Further, for each sample, the DR type was assigned based on the results. The results are also tabulated below.

TABLE 1A

| Sample | | 62 | K | W |
|---|---|---|---|---|
| Sequence | 1 | 0.11 | 0.10 | 0.10 |
| | 2 | 2.32 | 0.15 | 0.13 |
| | 3 | 0.16 | 1.99 | 0.17 |
| | 4 | 0.13 | 1.10 | 0.12 |
| | 5 | 0.11 | 0.11 | 0.11 |
| | 21 | 0.14 | 0.42 | 0.43 |
| | 7 | 0.11 | 0.97 | 1.49 |
| | 8 | 0.15 | 0.15 | 0.15 |
| | 9 | 0.10 | 0.11 | 0.11 |
| | 10 | 1.36 | 0.15 | 0.14 |
| | 11 | 0.12 | 0.12 | 0.12 |
| | 12 | 0.10 | 0.36 | 0.62 |
| | 13 | 0.16 | 0.19 | 0.15 |
| | 14 | 0.13 | 0.13 | 0.13 |
| | 15 | 0.11 | 0.12 | 1.50 |
| | 16 | 1.11 | 1.31 | 1.78 |
| DR type | | (1501–1503/ 1601, 0901) | (0301–0303, 0401/0403– 0411/1410) | (1301/1302/ 1304, 1301– 1307/1401/ 1402/1405/1409) |

Example 2

The procedure of Example 1 was repeated, except that different samples were used. The results are tabulated below. Further, for each sample, the DR type was assigned based on the results. The results are also tabulated below.

TABLE 2

| Sample | | OKB17 | OKB35 | N |
|---|---|---|---|---|
| Sequence | 1 | 0.11 | 0.33 | 2.37 |
| | 2 | 0.19 | 3.00 | 0.15 |
| | 3 | 0.29 | 1.15 | 0.19 |
| | 4 | 1.13 | 0.17 | 0.14 |
| | 5 | 0.12 | 0.13 | 0.13 |
| | 21 | 0.13 | 0.18 | 0.15 |
| | 7 | 0.11 | 0.11 | 0.95 |
| | 8 | 2.06 | 0.19 | 0.14 |
| | 9 | 0.12 | 0.12 | 1.25 |
| | 10 | 0.15 | 0.39 | 0.16 |
| | 11 | 0.12 | 1.95 | 0.12 |
| | 12 | 0.11 | 0.12 | 0.10 |
| | 13 | 0.24 | 0.20 | 1.32 |
| | 14 | 0.11 | 0.13 | 0.12 |
| | 15 | 0.10 | 0.10 | 0.10 |
| | 16 | 2.22 | 2.07 | 1.99 |
| DR type | | (0401/0403– 0411/1410, 0701) | (1501–1503/ 1601, 1001) | (0101/0102, 0801/0804) |

Example 3

For each of sequence 6 (SEQ ID NO: 6), sequence 21 (SEQ ID NO: 35), sequence 22 (SEQ ID NO: 36), sequence 23 (SEQ ID NO: 37), and sequence 24, a single-stranded DNA containing a sequence obtained by repeating about 50 copies the sequence was prepared according to a method disclosed in Japanese Patent Laid-Open No. 192198/1993.

Each single-stranded DNA thus prepared was immobilized on a microtiter plate as follows. The single-stranded DNA was first dissolved in a solution of 0.75M sodium chloride, 0.15M Tris-HCl, and 0.15M magnesium chloride (pH 8.0) to prepare a 4 μg/ml single-stranded DNA solution. The single-stranded DNA solution was added to a microtiter plate in an amount of 100 μl per well. The plate was covered, incubated at 37° C. for 16 hr, and washed three times with a buffer (1M sodium chloride, 0.1M Tris-HCl, 2 mM magnesium chloride, 0.1% Tween 20 (pH 9.3)).

Amplification was carried out 35 cycles by PCR, using DNAs extracted from human leukocytes as samples and the sequences 17 (SEQ ID NO: 39) and 18 (SEQ ID NO: 40) labeled with biotin at the 5' termini as primers. After the amplicon was denatured by heat, 5 μl of the denatured product was added to the wells, on which the single-stranded DNA was immobilized, containing 100 μl of a hybridization solution, and the wells were incubated at 58° C. for 1 hr. The solution was discarded, and 200 μl of a 3M tetramethylammonium chloride solution at 65° C. was added to the wells, and the wells were incubated at 65° C. for 5 min. The solution was discarded, and 200 μl of a 3M tetramethylammonium chloride solution at 65° C. was added to the wells again, and the wells were incubated at 65° C. for 10 min. The solution was discarded, and the wells were washed three times with 200 μl of an enzyme diluent (0.3M sodium chloride, 0.1M Tris-HCl, 2 mM magnesium chloride, 0.05% Tween 20 (pH 7.5)). The solution was discarded, 100 μl of an alkaline phosphatase-labeled avidin (BRL) diluted 2000 times with an enzyme diluent was added to the wells, and the wells were incubated at room temperature for 15 min. The solution was discarded, and the wells were washed three times with 200 μl of an enzyme diluent. A chromogenic substrate solution (4 mg p-nitrophenylphosphoric acid, 1M diethanolamine, 0.5 mM magnesium chloride (pH 9.8)) was added to the wells, and a reaction was allowed to proceed at room temperature for 60 min. Thereafter, the absorbance was measured at 405 nm.

The results of the measurement of the absorbance for each sequence are tabulated below.

TABLE 3

| Sample | DRB1 type | Sequence | | | | |
|---|---|---|---|---|---|---|
| | | 6 | 21 | 22 | 23 | 24 |
| 22 | 1201,0801 | 1.50 | 1.37 | 0.53 | 0.12 | 0.08 |
| 65 | 0901,1201 | 1.49 | 1.21 | 0.41 | 0.15 | 0.24 |
| 69 | 0403,1201 | 1.88 | 1.68 | 0.26 | 0.16 | 0.11 |
| 107 | 0803,1201 | 1.06 | 0.75 | 0.29 | 0.11 | 0.07 |
| 108 | 0101,0406 DRB4*0101 | 0.11 | 0.13 | 0.36 | 0.06 | 0.05 |
| 64 | 1502,1403 DRB3*0101 | 0.25 | 0.18 | 0.54 | 0.12 | 0.10 |
| 121 | 0901,1403 DRB3*0101 | 0.02 | 0.14 | 0.38 | 0.01 | 0.00 |
| 117 | 0901,1101 DRB3*0202 | 0.02 | 0.27 | 0.92 | 0.01 | 0.02 |

Example 4

The procedure of Example 3 was repeated, except that sequences 6 (SEQ ID NO: 6) and 21 (SEQ ID NO: 40) alone were used and that samples specified in Table 4 included some samples used in Example 3.

The absorbances for each sequence are tabulated below.

TABLE 4

| Sample | DRB1 type | Sequence | |
|---|---|---|---|
| | | 6 | 21 |
| 22 | 1201,0801 | 0.62 | 0.46 |
| 69 | 0403,1201 | 0.45 | 0.40 |
| 107 | 0803,1201 | 1.00 | 0.96 |
| 92 | 1502,1101 | 0.14 | 0.20 |
| 93 | 0405,1101 | 0.10 | 0.23 |
| 117 | 0901,1101 DRB3*0202 | 0.11 | 0.18 |
| 118 | 1101,1405 | 0.14 | 0.22 |
| 64 | 1502,1403 DRB3*0101 | 0.14 | 0.10 |

Example 5

For each of sequence 5 (SEQ ID NO: 5), sequence 5a (SEQ ID NO: 21), sequence 19 (SEQ ID NO: 33), sequence 19a, and sequence 20, a single-stranded DNA containing a sequence obtained by repeating about 50 copies the sequence was prepared according to a method disclosed in Japanese Patent Laid-Open No. 192198/1993.

Each single-stranded DNA thus prepared was immobilized on a microtiter plate as follows. The single-stranded DNA was first dissolved in a solution of 0.75M sodium chloride, 0.15M Tris-HCl, and 0.15M magnesium chloride (pH 8.0) to prepare a 4 µg/ml single-stranded DNA solution. The single-stranded DNA solution was added to a microtiter plate in an amount of 100 µl per well. The plate was covered, incubated at 37° C. for 16 hr, and washed three times with a buffer (1M sodium chloride, 0.1M Tris-HCl, 2 mM magnesium chloride, 0.1% Tween 20 (pH 9.3)).

Amplification was carried out 35 cycles by PCR, using DNAs extracted from human leukocytes as samples and the sequences 17 and 18 labeled with biotin at the 5'termini as primers. After the amplicon was denatured by heat, 5 µl of the denatured product was added to the wells, on which the single-stranded DNA was immobilized, containing 100 µl of a hybridization solution, and the wells were incubated at 58° C. for 1 hr. The solution was discarded, and 200 µl of a 3M tetramethylammonium chloride solution at 65° C. was added to the wells, and the wells were incubated at 65° C. for 5 min. The solution was discarded, and 200 µl of a 3M tetramethylammonium chloride solution at 65° C. was added to the wells again, and the wells were incubated at 65° C. for 10 min. The solution was discarded, and the wells were washed three times with 200 µl of an enzyme diluent (0.3M sodium chloride, 0.1M Tris-HCl, 2 mM magnesium chloride, 0.05% Tween 20 (pH 7.5)). The solution was discarded, 100 µl of an alkaline phosphatase-labeled avidin (BRL) diluted 2000 times with an enzyme diluent was added to the wells, and the wells were incubated at room temperature for 15 min. The solution was discarded, and the wells were washed three times with 200 µl of an enzyme diluent. A chromogenic substrate solution (4 mg p-nitrophenylphosphoric acid, 1M diethanolamine, 0.5 mM magnesium chloride (pH 9.8)) was added to the wells, and a reaction was allowed to proceed at room temperature for 60 min. Thereafter, the absorbance was measured at 405 nm.

The absorbance for each sequence are tabulated below.

TABLE 5

| Sample | DRB1 type | Sequence | | | | |
|---|---|---|---|---|---|---|
| | | 5 | 5a | 19 | 19a | 20 |
| JRC30 | | 0.855 | 0.413 | 0.588 | 0.485 | 0.321 |
| 69 | 0403,1201 | 0.117 | 0.091 | 0.203 | 0.109 | 0.095 |
| 93 | 0405,1101 | 0.552 | 0.254 | 0.398 | 0.283 | 0.209 |
| 118 | 1101,1405 | 0.582 | 0.439 | 0.804 | 0.365 | 0.395 |

Example 6

The procedure of Example 5 was repeated, except that sequence 5 (SEQ ID NO: 5), sequence 19 (SEQ ID NO: 33), and sequence 20 (SEQ ID NO: 34) alone were used and that samples specified in Table 6 included some samples used in Example 5.

The absorbances for each sequence are tabulated below.

TABLE 6

| Sample | DRB1 type | Sequence | | |
|---|---|---|---|---|
| | | 5 | 19 | 20 |
| 23 | 0901 | 0.022 | 0.057 | 0.075 |
| 63 | 0403 | 0.026 | 0.171 | 0.041 |
| 92 | 1502,1101 | 0.461 | 0.392 | 0.194 |
| 93 | 0405,1101 | 0.515 | 0.513 | 0.266 |
| 117 | 0901,1101 | 0.538 | 0.470 | 0.375 |
| 118 | 1101,1405 | 0.421 | 0.393 | 0.310 |
| K | 0301,0403 | 0.040 | 0.184 | 0.022 |

Example 7

For each of 16 sequences specified in the following Table 7, a single-stranded DNA containing a sequence obtained by repeating about 50 copies the sequence specified in the table was prepared according to a method disclosed in Japanese Patent Laid-Open No. 192198/1993.

Each single-stranded DNA thus prepared was immobilized on a microtiter plate as follows. The single-stranded DNA was first dissolved in a solution of 0.75M sodium chloride, 0.15M Tris-HCl, and 0.15M magnesium chloride (pH 8.0) to prepare a 4 µg/ml single-stranded DNA solution. The single-stranded DNA solution was added to a microtiter plate in an amount of 100 µl per well. The plate was covered, incubated at 370° C. for 16 hr, and washed three times with a buffer (1M sodium chloride, 0.1M Tris-HCl, 2 mM magnesium chloride, 0.1% Tween 20 (pH 9.3)).

Amplification was carried out 30 cycles by PCR, using DNAs extracted from human leukocytes as samples and the sequences 17 and 18 labeled with biotin at the 5'termini as primers. After the amplicon was denatured by heat, 5 µl of the denatured product was added to the wells, on which the single-stranded DNA was immobilized, containing 100 µl of a hybridization solution, and the wells were incubated at 58° C. for 1 hr. The solution was discarded, and 200 µl of a 3M tetramethylammonium chloride solution at 650° C. was added to the wells, and the wells were incubated at 65° C. for 5 min. The solution was discarded, and 200 µl of a 3M tetramethylammonium chloride solution at 65° C. was added to the wells again, and the wells were incubated at 650° C. for 10 min. The solution was discarded, and the wells were washed three times with 300 µl of an enzyme diluent (0.3M sodium chloride, 0.1M Tris-HCl, 2 mM magnesium chloride, 0.05% Tween 20 (pH 7.5)). The solution was discarded, 100 µl of a peroxidase-labeled avidin diluted 5000 times with an enzyme diluent was added to the wells, and the wells were incubated at room temperature for 15 min. The solution was discarded, and the wells were washed three times with 300 µl of an enzyme diluent. A chromogenic substrate solution (1.5 mM 2,2'-adino-bis-(3-ethylbenzothiazoline-6-sulfonic acid)diammonium, a 0.2M tartrate buffer containing 0.015% $H_2O_2$ (pH 4.4)) was added to the wells, and a reaction was allowed to proceed at room temperature for 15 min. Thereafter, the absorbance was measured at 415 nm.

The results of the measurement of the absorbance for each sequence are tabulated below. Further, for each sample, the DR type was assigned based on the results. The results are also tabulated below.

TABLE 7

| Sample | | N | O |
|---|---|---|---|
| Sequence | 1 | 3.58 | 0.03 |
| | 2 | 0.13 | 0.05 |
| | 3 | 0.18 | 0.10 |
| | 4 | 0.09 | 0.03 |
| | 5 | 0.09 | 0.03 |
| | 6 | 0.12 | 2.36 |
| | 7 | 1.20 | 1.13 |
| | 8 | 0.11 | 0.04 |
| | 9 | 2.13 | 0.04 |
| | 10 | 0.20 | 0.05 |
| | 11 | 0.09 | 0.04 |
| | 12 | 0.03 | 0.43 |
| | 13 | 1.57 | 1.72 |
| | 14 | 0.04 | 0.06 |
| | 15 | 0.02 | 1.24 |
| | 16 | 2.77 | 3.27 |
| DR type | | (0101/0102, 0801/0804) | (1201/1202, 1301/1302/1304) |

Example 8

For each of DRB3705' (AGCTCCTGCGCTTCGACAGC, SEQ ID NO: 41), which is a sequence selected from those described in Tissue Antigens, Vol. 46, No.3-II, p262, (1995), and sequence 6' (AGCTACTGCGCTTCGACAGC) (probe 6', SEQ ID NO: 42) according to the present invention, a single-stranded DNA containing a sequence obtained by repeating about 50 times the sequence was prepared according to a method disclosed in Japanese Patent Laid-Open No. 192198/1993. Each single-stranded DNA thus prepared was immobilized on a microtiter plate as follows.

The single-stranded DNA was first dissolved in a solution of 0.75M sodium chloride, 0.15M Tris-HCl, and 0.15M magnesium chloride (pH 8.0) to prepare a 0.4 µg/ml single-stranded DNA solution. The single-stranded DNA solution was added to a microtiter plate in an amount of 100 µl per well. The plate was covered, incubated at 37° for 16 hr, and washed three times with a buffer (1M sodium chloride, 0.1M Tris-HCl, 2 mM magnesium chloride, 0.1% Tween 20 (pH 9.3)).

Amplification was carried out 30 cycles by PCR, using HLA-DR type DNAs extracted from human leukocytes as samples (#22, #69, #107, #121, #35, #93, and #118) and DRB3705' and probe 6' of the present invention labeled at the 5' end with biotin as primers. The resulting amplified product was denatured by heat, 5 µl of the denatured product was added to the wells, with the single-stranded DNA immobilized thereon, containing 100 µl of a hybridization solution, and the wells were incubated at 58° C. for one hour. The liquid was discarded, and 200 µl of a 3M tetramethylammonium solution at 65° C. was added to the wells, and the wells were incubated at 65° C. for 5 min. The liquid was discarded, and 200 µl of a 3M tetramethylammonium solution at 65° C. was again added to the wells, and the wells were incubated at 65° C. for 10 min. The liquid was discarded, and the wells were washed three times with 300 µl of an enzyme diluent (0.3M sodium chloride, 0.1M Tris-HCl, 2 mM magnesium chloride, 0.05% Tween 20 (pH 7.5)). The liquid was discarded, 100 µl of a peroxidase-labeled avidin diluted 5000 times with an enzyme diluent was added to the wells, and the wells were incubated at room temperature for 15 min. The liquid was discarded, and the wells were washed three times with 300 µl of an enzyme diluent. A chromogenic substrate solution (1.5 mM 2,2'-adino-bis-(3-ethylbenzothiazoline-6-sulfonic acid) diammonium, a 0.2M tartrate buffer containing 0.015% $H_2O_2$ (pH 4.4)) was added to the wells, and a reaction was allowed to proceed at room temperature for 15 min. Thereafter, the absorbance was measured at 415 nm. The results of the measurement of the absorbance for each sequence are tabulated below.

| Sample (DR type) | DRB3705' | Probe 6' |
|---|---|---|
| #22(DR12/DR8) | 1.20 | 1.27 |
| #69(DR4/DR12) | 1.61 | 1.35 |
| #107(DR8/DR12) | 1.75 | 1.80 |
| #121(DR9/DR14) | 0.16 | 0.05 |
| #35(DR4/DR14) | 0.38 | 0.09 |
| #93(DR4/DR11) | 0.46 | 0.12 |
| #118(DR11/DR14) | 0.35 | 0.06 |

The results show that probe 6' of the present invention, prepared by inserting mutation (C→A) into one base of DRB3705', does not hybridize to the DR11 or DR14 samples and that the mutation hardly affects the hybridization to the DR12 samples.

We claim:
1. An oligonucleotide probe comprising the sequence AGCTACTGCGCTTCGACAGC (SEQ ID NO: 42).

* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:1:

CGGTTGCTGG AAAGATGCAT C                                  21

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:2:

ACACTCCCTC TTAGGCTG                                    18

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:3:

GGCCGGGTGG ACAACTAC                                    18

(2) INFORMATION FOR SEQ ID NO:4:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:4:

ATGTTTAACC TGCTCCAA                                    18

(2) INFORMATION FOR SEQ ID NO:5:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:5:

CCTGATGAGG AGTACTGGAA                                               20

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

AGCTACTGCG CTTCGAC                                                  17

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:7:

CGTAGAGTAC TCCAAGAA                                                 18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:8:

CTTATACTTA CCCTGCCA                                                 18

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:9:

AGACAGGCGG GCCCT                                                    15

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO:10:

TCAAACTTAT CCTGCTTC                                                     18

(2) INFORMATION FOR SEQ ID NO:11:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO:11:

AAACTTAACC TCCTCCAA                                                     18

(2) INFORMATION FOR SEQ ID NO:12:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO:12:

ACTCTACGTC TGAGTGTC                                                     18

(2) INFORMATION FOR SEQ ID NO:13:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO:13:

ACGGGTGAGT GTTATTTC                                                     18

(2) INFORMATION FOR SEQ ID NO:14:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO:14:

GACCTCCTGG AAGACAGG                                                     18

(2) INFORMATION FOR SEQ ID NO:15:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:15:

ACATCCTGGA AGACGAGC                                                       18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:16:

CCCGTAGTTG TGTCTGCA                                                       18

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:17:

GATGCATCTT TCCAGCAACC G                                                   21

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:18:

CAGCCTAAGA GGGAGTGT                                                       18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:19:

GTAGTTGTCC ACCCGGCC                                                       18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:20:

TTGGAGCAGG TTAAACAT                                                 18

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:21:

TTCCAGTACT CCTCATACGG                                               20

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:22:

GTCGAAGCGC AGTAGCT                                                  17

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:23:

TTCTTGGAGT ACTCTACG                                                 18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:24:

TGGCAGGGTA AGTATAAG                                                 18

(2) INFORMATION FOR SEQ ID NO:25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO:25:

AGGGCCCGCC TGTCT                                                    15

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:26:

GAAGCAGGAT AAGTTTGA                                                 18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:27:

TTGGAGGAGG TTAAGTTT                                                 18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:28:

TGCAGACACA ACTACGGG                                                 18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:29:

GACACTCAGA CGTAGAGT                                                 18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:30:

GAAATAACAC TCACCCGT                                                    18

(2) INFORMATION FOR SEQ ID NO:31:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:31:

CCTGTCTTCC AGGAGGTC                                                    18

(2) INFORMATION FOR SEQ ID NO:32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:32:

GCTCGTCTTC CAGGATGT                                                    18

(2) INFORMATION FOR SEQ ID NO:33:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:33:

CCTGATGAGG AGTACTGGAA CAG                                              23

(2) INFORMATION FOR SEQ ID NO:34:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:34:

TGATGAGGAG TACTGGAA                                                    18

(2) INFORMATION FOR SEQ ID NO:35:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:35:

AGTGTCTCTC CAGTAACC                                                        18

(2) INFORMATION FOR SEQ ID NO:36:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:36:

AGCCCCTGCG CTTCGAC                                                         17

(2) INFORMATION FOR SEQ ID NO:37:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:37:

AGCTCATGCG CTTCGAC                                                         17

(2) INFORMATION FOR SEQ ID NO:38:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:38:

AGCTCCAGCG CTTCGAC                                                         17

(2) INFORMATION FOR SEQ ID NO:39:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "SYNTHETIC DNA"

(xi) SEQUENCE DESCRIPTION: SEQ ID NO:39:

CCGCTGCACT GTGAAGCTCT                                                      20

(2) INFORMATION FOR SEQ ID NO:40:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO:40:

TCGTGTCCCC ACAGCACGT                                                            19

(2) INFORMATION FOR SEQ ID NO:41:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO:41:

AGCTCCTGCG CTTCGACAGC                                                           20

(2) INFORMATION FOR SEQ ID NO:42:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:42:

AGCTACTGCG CTTCGACAGC                                                           20